United States Patent
Hufford et al.

(10) Patent No.: US 12,193,772 B2
(45) Date of Patent: Jan. 14, 2025

(54) DETERMINING RELATIVE ROBOT BASE POSITIONS USING EXTERNALLY POSITIONED IMAGERS

(71) Applicant: Asensus Surgical US, Inc., Durham, NC (US)

(72) Inventors: Kevin Andrew Hufford, Cary, NC (US); Federico Campisano, Timnath, CO (US); Lior Alpert, Haifa (IL)

(73) Assignee: Asensus Surgical US, Inc., Durham, NC (US)

( * ) Notice: Subject to any disclaimer, the term of this patent is extended or adjusted under 35 U.S.C. 154(b) by 149 days.

(21) Appl. No.: 17/944,170

(22) Filed: Sep. 13, 2022

(65) Prior Publication Data

US 2023/0080041 A1    Mar. 16, 2023

Related U.S. Application Data

(60) Provisional application No. 63/294,765, filed on Dec. 29, 2021, provisional application No. 63/243,716, filed on Sep. 13, 2021.

(51) Int. Cl.
*A61B 34/30* (2016.01)
*A61B 34/20* (2016.01)
*A61B 90/00* (2016.01)

(52) U.S. Cl.
CPC .............. *A61B 34/30* (2016.02); *A61B 34/20* (2016.02); *A61B 90/37* (2016.02); *A61B 2034/2055* (2016.02); *A61B 2034/305* (2016.02)

(58) Field of Classification Search
CPC ......... A61B 34/30; A61B 34/20; A61B 90/37; A61B 2034/2055; A61B 2034/305; A61B 90/361; A61B 2017/00216; A61B 2034/2059; A61B 2034/2065; A61B 2090/3945; A61B 2090/3979; A61B 2560/0437

See application file for complete search history.

(56) References Cited

U.S. PATENT DOCUMENTS

| | | |
|---|---|---|
| 2007/0005045 A1 | 1/2007 | Mintz et al. |
| 2007/0083098 A1 | 4/2007 | Stern et al. |
| 2012/0307027 A1 | 12/2012 | Popovic et al. |
| 2013/0066335 A1 | 3/2013 | Barwinkel et al. |
| 2014/0083058 A1* | 3/2014 | Issing ............... B65B 35/30 53/473 |
| 2015/0297313 A1 | 10/2015 | Reiter et al. |
| 2017/0079722 A1 | 3/2017 | O'Grady et al. |
| 2017/0333137 A1 | 11/2017 | Roessler |
| 2019/0069962 A1* | 3/2019 | Tabandeh ............... A61B 34/25 |
| 2021/0153958 A1* | 5/2021 | Meglan ................. A61B 90/36 |
| 2022/0117680 A1* | 4/2022 | Tabandeh .............. A61B 17/34 |
| 2023/0270511 A1* | 8/2023 | Junio ................... B25J 9/1697 700/248 |

OTHER PUBLICATIONS

Non-Final Office Action dated Aug. 17, 2022 for co-pending U.S. Appl. No. 16/733,200.

* cited by examiner

*Primary Examiner* — Alexei Bykhovski

(57) ABSTRACT

A system for determining relative positions of subsystems of a robot-assisted surgical system includes a subsystem component including a plurality of manipulator arms and a surgeon console. Each subsystem component includes at least one of an optical tracker and a light emitter. Image data from the optical trackers is analyzed to determine the relative positions of the subsystems.

13 Claims, 7 Drawing Sheets

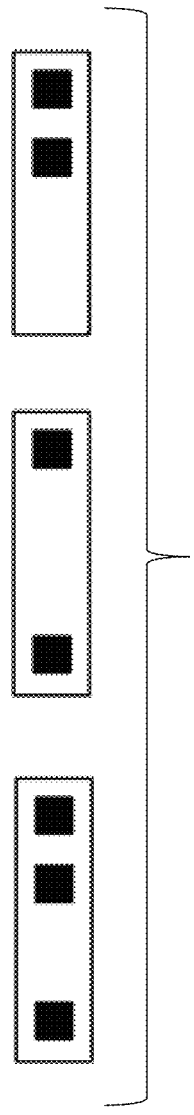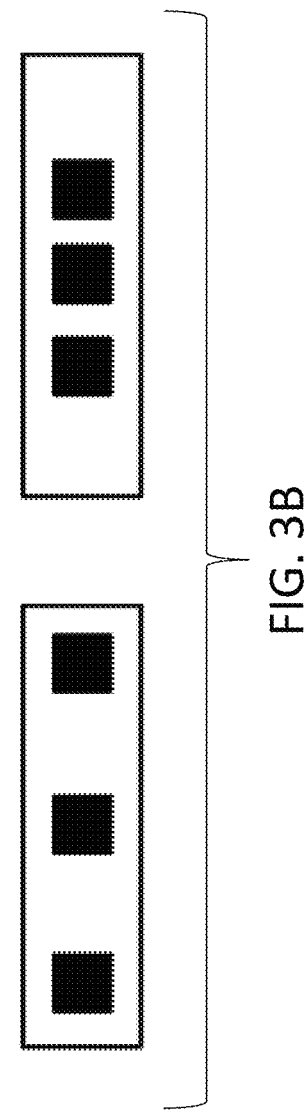
FIG. 3A
FIG. 3B

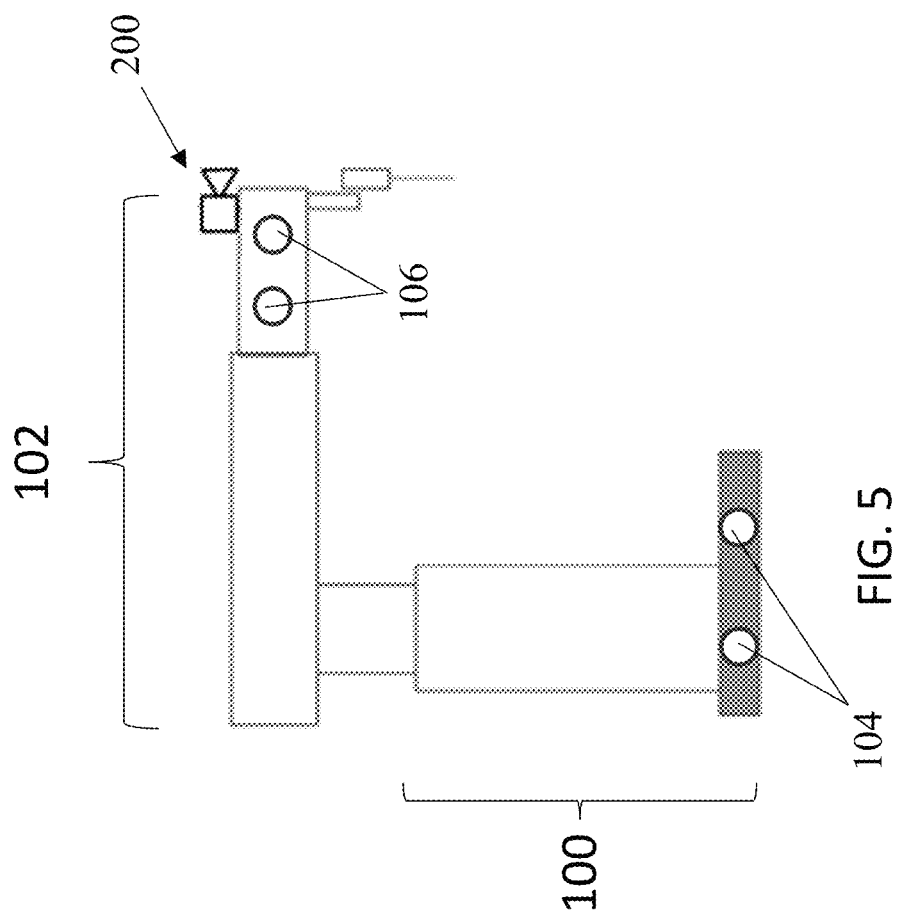

DETERMINING RELATIVE ROBOT BASE POSITIONS USING EXTERNALLY POSITIONED IMAGERS

This application claims the benefit of US Provisional Nos. 63/243,716, filed Sep. 13, 2021, and 63/294,765, filed Dec. 29, 2021.

BACKGROUND

In robotic surgery, for coordinated motion between arms, or for automatic movements, it is often necessary to understand the relative positioning between robotic arms. For surgical robots having multiple arms that emanate from a common base, acquiring the relative position can be performed simply based on known kinematics. For surgical robotic systems in which the robotic arms are mounted on separate carts that may be individually moved, acquiring the relative positioning is more difficult.

The described invention is a system and method for determining the relative positioning of subsystem components of a surgical robotic system using computer vision, such as one or more manipulator arms, a surgeon console, and/or patient bed. The disclosed system is one that allows the relative positions of the subsystem components to be determined (i) in cases where all subsystems of the surgical robotic system are visible by a single camera, as well as in cases where not all subsystems may be seen by a single camera, but in which case multiple camera instances may be used to determine the relative positions.

Although the inventions described herein may be used on a variety of robotic surgical systems, the embodiments will be described with reference to a system of the type shown in FIG. 1. In the illustrated system, a surgeon console 12 has two input devices such as handles 17, 18 that the surgeon selectively assigns to two of the robotic manipulators 13, 14, 15, allowing surgeon control of two of the surgical instruments 10a, 10b, and 10c disposed at the working site at any given time. To control a third one of the instruments disposed at the working site, one of the two handles 17, 18 is operatively disengaged from one of the initial two instruments and then operatively paired with the third instrument. A fourth robotic manipulator, not shown in FIG. 1, may support and maneuver an additional instrument.

One of the instruments 10a, 10b, 10c is a laparoscopic camera that captures images for display on a display 23 at the surgeon console 12. The camera may be moved by its corresponding robotic manipulator using input from an eye tracker 21, or using input from one of the input devices 17, 18.

The input devices at the console may be equipped to provide the surgeon with tactile feedback so that the surgeon can feel on the input devices 17, 18 the forces exerted by the instruments on the patient's tissues.

In use, a surgeon positioned at the console 12 uses the input devices 17, 18 and, where applicable, the eye tracker 21, to give input to the system to move the instruments and/or camera. A control unit 30 is operationally connected to the robotic arms and to the user interface. The control unit receives user input from the input devices corresponding to the desired movement of the surgical instruments and/or camera, and the robotic arms are caused to manipulate the surgical instruments/camera accordingly.

In this embodiment, each arm 13, 14, 15 is separately positionable within the operating room during surgical set up. In other words, the bases of the arms are independently moveable across the floor of the surgical room. The patient bed 2 is likewise separately positionable. This configuration differs from other systems that have multiple manipulator arms on a common base, so that the relative positions of the arms can be kinematically determined by the system.

Commonly owned US Publication No. US 2020/0205911, which is incorporated by reference, describes use of computer vision to determine the relative positions of manipulator bases within the operating room. As described in that application, one or more cameras are positioned to generate images of a portion of the operating room, including the robotic manipulators, or instruments carried by the robotic manipulators. Image processing is used to detect the robotic system components on the images captured by the camera. Once the components are detected in the image for each manipulator, the relative positions of the bases within the room may be determined. Concepts described in that application are relevant to the present disclosure and may be combined with the features or steps disclosed in this application.

In some arrangements of manipulators and other components and personnel within an operating room, certain components may be occluded from the view of a camera capturing images within the operating room for use in determining relative manipulator base positions. This application also describes systems and methods for allowing for determining the relative positions of the arms and, optionally, the surgeon console 12 and/or patient bed, even where one or more of the components whose position is to be determined is blocked from the view of one or more of the cameras.

BRIEF DESCRIPTION OF THE DRAWINGS

FIG. 3A schematically illustrates three emitter arrays displaying different emitter patterns.

FIG. 3B schematically illustrates a pair of emitter arrays having different emitter spacings.

FIG. 5 is a side elevation view of a robotic manipulator showing one example of optical tracker and emitter placements.

DETAILED DESCRIPTION

Concepts described this application allow the relative positions of bases of robotic arms and optionally other robotic system components within an operating room (e.g., the patient bed and/or surgeon console) to be determined. This information is useful for certain operations of the robotic system, including coordinated motion between the manipulators arms, or for automatic movements, or for collision avoidance interventions. This is particularly beneficial where components of the system are not physically linked, such as where the robotic manipulator arms and patient bed are independently positionable (e.g., their bases are independently moveable between different positions along the floor of the operating room).

Figure 1:
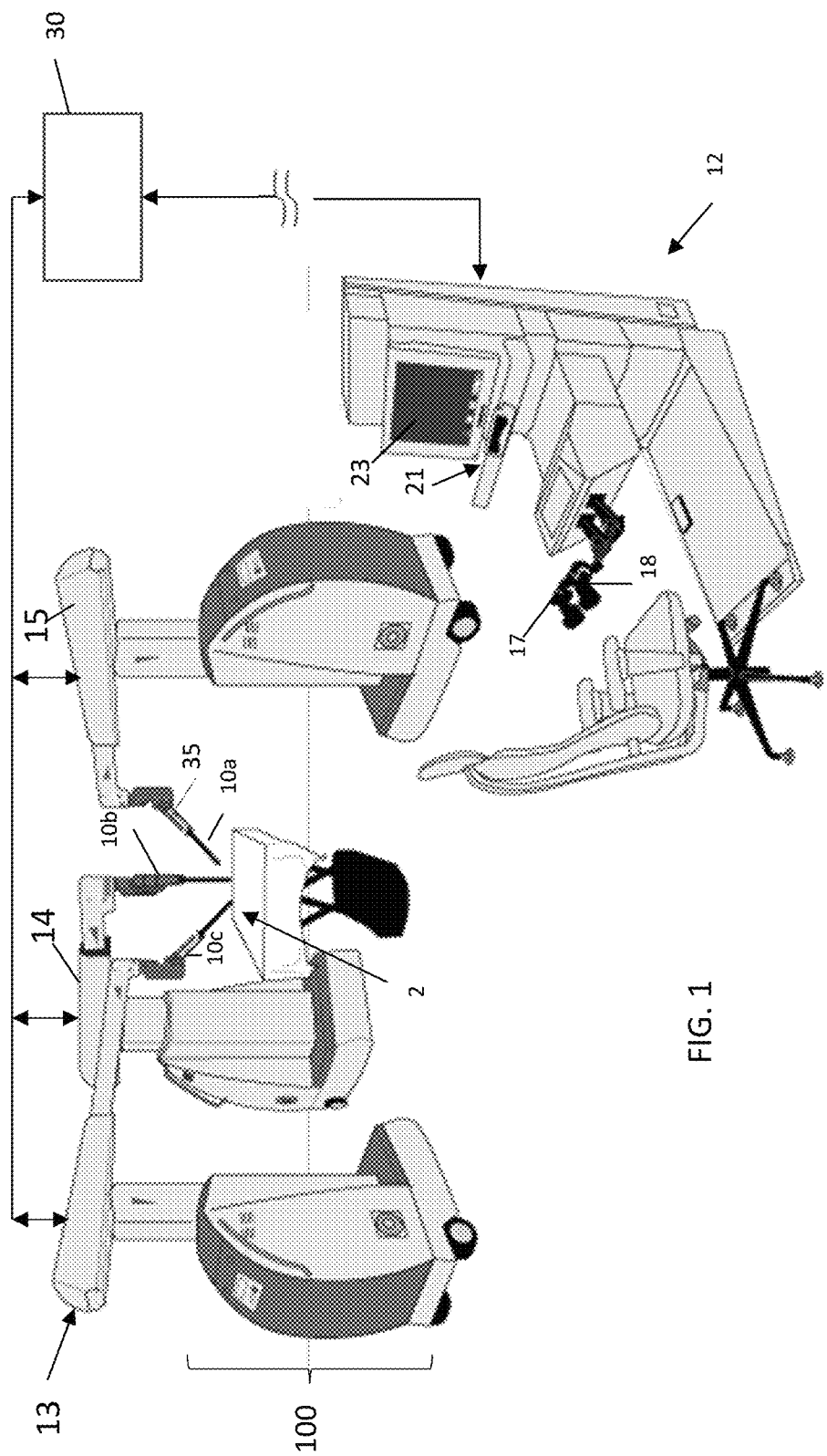
FIG. 1 illustrates a surgical robotic system that may incorporate methods and modes of operation described herein.
Figure 2:
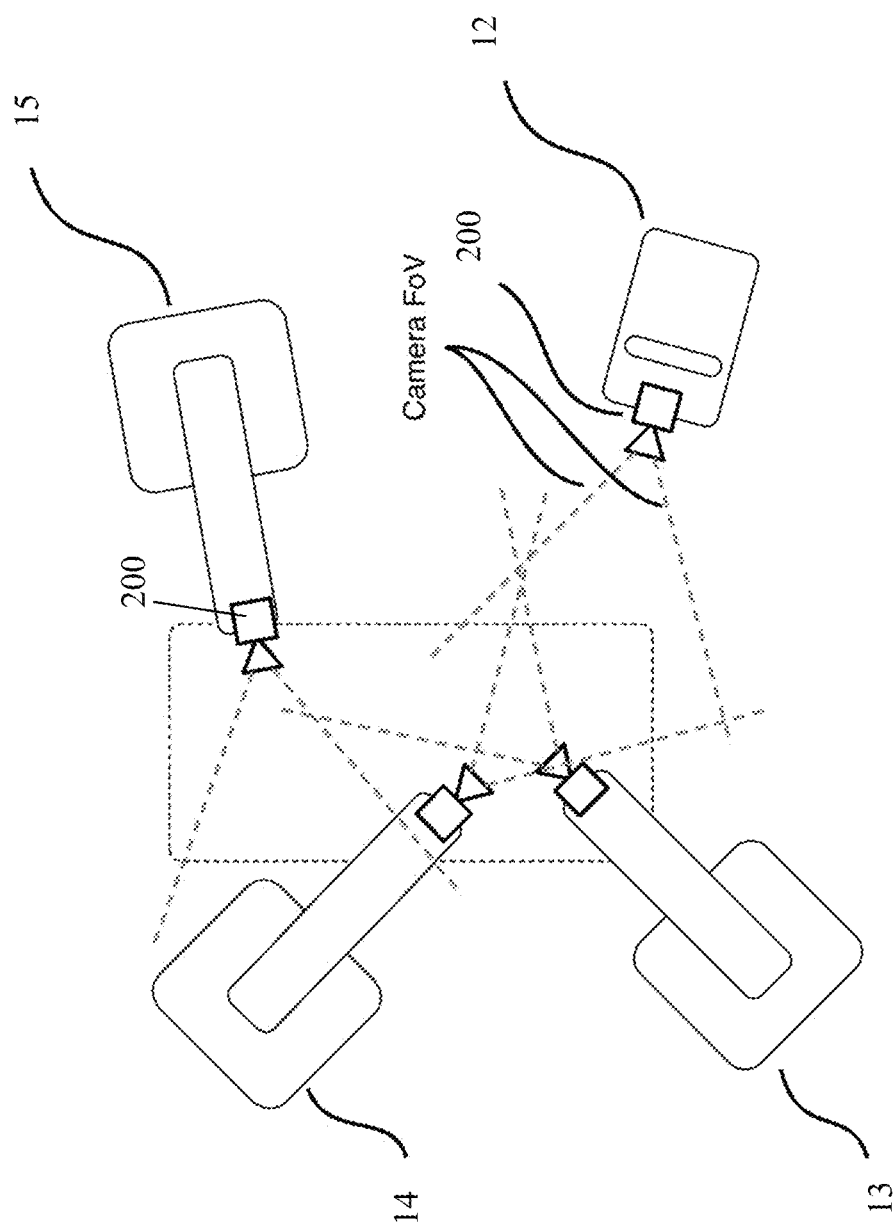
FIG. 2 shows a top plan view of an operating room using optical trackers and emitters to determine relative positions of subsystem components.

Referring to FIG. 2, an exemplary system includes one or more manipulator arms 13, 14, 15, and a surgeon console 12. In this application, these components may be referred to generically as "subsystems." The subsystems are shown positioned relative to a patient bed. As shown, the console 12 and manipulator arms 13, 14, 15 are independently positionable and thus may be relocated to different areas of the operating room independent of one another, such as by unlocking their wheels and rolling them to a new position.

Optical tracking is used to determine the relative positions of the subsystems. Each sub-system will have at least one light emitter or set of light emitters, or at least one camera (which may be alternatively referred to as a tracking sensor, imager or tracker), or both light emitter(s) and a camera in order to allow determination of the relative position of each sub-system related to all the others. In the FIG. 2 embodiment, a camera 200 is shown mounted on each subsystem. An emitter or set of emitters (not shown in FIG. 2 but see FIG. 5) is also mounted in a similar location on each subsystem. The emitters may be configured to emit wavelengths in either or both the infrared (IR) and visible light spectrums. In preferred embodiments, the emitters are IR transmitters, but visible light emitters or other wavelengths or combinations of wavelengths are within the scope of this disclosure.

If the distance between two emitters fixably mounted to a single subsystem component is known a priori, then the distance from a camera viewing those emitters may be calculated using triangulation.

The camera field-of-view (FoV) of each camera is identified in FIG. 2 using dashed lines. The camera on the console 12 has a FoV that allows it to "see" arm 14 and arm 13, but arm 15 is outside of its field of view. However, arm 15 is within the FoV of the camera on arm 13, and thus the relative coordinate system transformations between each subsystem may be known, and their position in a "global" coordinate system may be known as well. The relevant global coordinate system may reference the console 12, the OR table, the patient umbilicus (which in some cases may be the planned or likely location for the port/trocar through which the endoscopic camera will be inserted), or some other relevant location within the operating room. Further tracking means and/or calculations may be performed to provide this information.

The processing of this relative positioning data may be accomplished in a few different ways:

In one embodiment, each subsystem may include a processor having a memory storing a computer program that includes instructions executable by the processor to receive image data corresponding to images captured by that subsystem's camera, to execute an algorithm to detect light from emitters of neighboring subsystems in the captured images, and to perform the relative position calculation of all subsystems that it can see in a coordinate system relative to itself. In this embodiment, the processor then publishes that data onto the network for other subsystems to digest, or then publish that data to some other processing unit that aggregates this information into an overall positioning calculation.

In other cases, the data from each camera may be sent (as raw image data, or as digitally processed data) to a central processing unit having a memory storing a computer program that includes instructions executable by the processor to receive the image data and to aggregate the raw data from each subsystem, and to then calculate the relative positioning of each base in an overall global coordinate system.

The emitters may be configured to allow the system to determine which subsystem a given emitter or emitter set or array is positioned on based on the received image data. Memory associated with the processor that determines the relative positioning stores information correlating the identifying characteristics of an emitter or emitter array with its corresponding subsystem component. There are many different ways in which the emitters or emitter arrays can be uniquely identifiable by the system. For example, relative distance between multiple emitters on a single subsystem may be used to differentiate between different subsystems or subsystem types. For instance, each subsystem might have a different pattern of emitter arrays. One such example is shown in FIG. 3A, which shows three emitter arrays, each having a different pattern. It should be noted that in some embodiments a different pattern may be achieved by positioning the emitters of each array in its unique pattern, whereas in another configuration the emitters one each subsystem may be arranged in identical patterns but illuminated so that only select ones of the emitters are illuminated to create the individual patterns. In other words, the three arrays of FIG. 3A might each consist of four emitters with uniform spacing, with the black squares showing which of the emitters are illuminated to create each individual pattern. Alternatively, each arm or subsystem may be differentiated by having different spacing between their respective IR emitters. See FIG. 3B. In other cases, common subsystems might have the same emitter arrangement. For example, in a robotic surgical system, a console may be differentiated from a robotic manipulator arm by their respective differences in emitter arrangement. Other means of differentiation may be emitters strobing or pulsing at different speeds and/or in different sequences, and/or emitting light at different wavelengths.

Figure 3C:
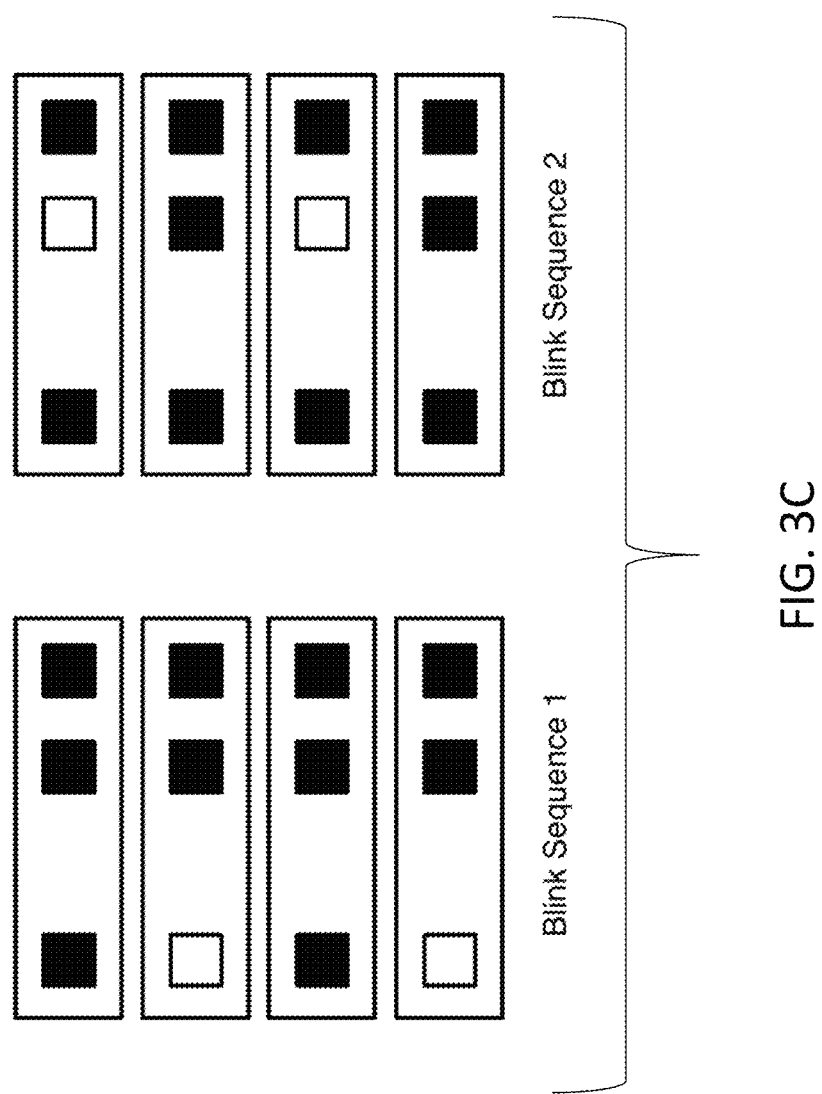
FIG. 3C schematically illustrates a pair of emitter arrays displaying different blink sequences.

In other embodiments, blink sequences may serve as differentiators. In FIG. 3C, for example, a black square denotes an emitter that is on, and a white square is an emitter that is off. These two blink sequences could be used to differentiate between different arms, or between types of subsystems, such one emitter set being mounted on an arm, and one being mounted on a console.

As discussed with respect to FIG. 3B, in some embodiments the distance between emitters in an emitter "set" or array may be different for different subsystems and may provide orientation and identification information by virtue of that information. This may be further enhanced by the use of differently-colored (e.g., LED) emitters, or even by color-changing emitters (such as RGB LEDs) which can be driven to provide many different colors, thus increasing the potential differentiation capability.

The described embodiment lends itself well to subsystem arrangements lacking in comprehensive visibility, i.e., where in may not be possible for a single camera/tracker's view to have overall coverage and be able to see every other subsystem's emitters as discussed with respect to FIG. 2. In such scenarios, the system can determine relative base positioning as long as there is a serial chain of visibility of subsystems. As long as each one subsystem's emitters are seen by at least one other subsystem's camera, the relative positioning of each subsystem may be determined. From there the system can perform a serial chain of coordinate system transformations, and the global position of each subsystem can be determined.

Although the FIG. 2 embodiment describes the system as being used to track the manipulator arms and, optionally, the console, they may be used to track other subsystems including various equipment or objects within the operating room (OR), including, without limitation:

The OR table base

The OR table top and its tilting surface

OR staff—any marker(s) or trackable objects worn by the OR staff (i.e., on a headlamp, mask, head covering, watch, wristband, etc.)

The patient, or any marker(s) or trocar(s) affixed or inserted into the patient

Moreover, emitters and/or tracking cameras may be positioned on any portion of the system or other features within the operating room, including the manipulator arms, surgeon console, boom lights, laparoscopic towers, cars, the ceiling, a floor mounted structure, the operating table, anesthesia equipment, IV stands, etc.

Emitter/Tracker Positioning

In some embodiments, some or all of the various subsystems of the surgical system may be equipped with multiple emitters (and/or trackers) to enhance visibility and enable robust tracking of the respective positions of the robotic system components.

To permit differentiation between different ones of the emitters on a single subsystem, each emitter on the subsystem may have differentiating features of the type described above, such as different blink sequences and/or colors or color patterns.

Using a stereo pair of trackers/cameras with a known distance between them viewing a single emitter, it is possible to determine the relative distance from the cameras to any emitter.

Using a single camera, viewing at least two emitters of known separation is also able to provide triangulation information.

If multiple emitters are installed around a robotic manipulator base, a tracker/camera/set of cameras is then able to determine the side of the manipulator arm in question simply by the IDs/emitters in view.

Figure 4:
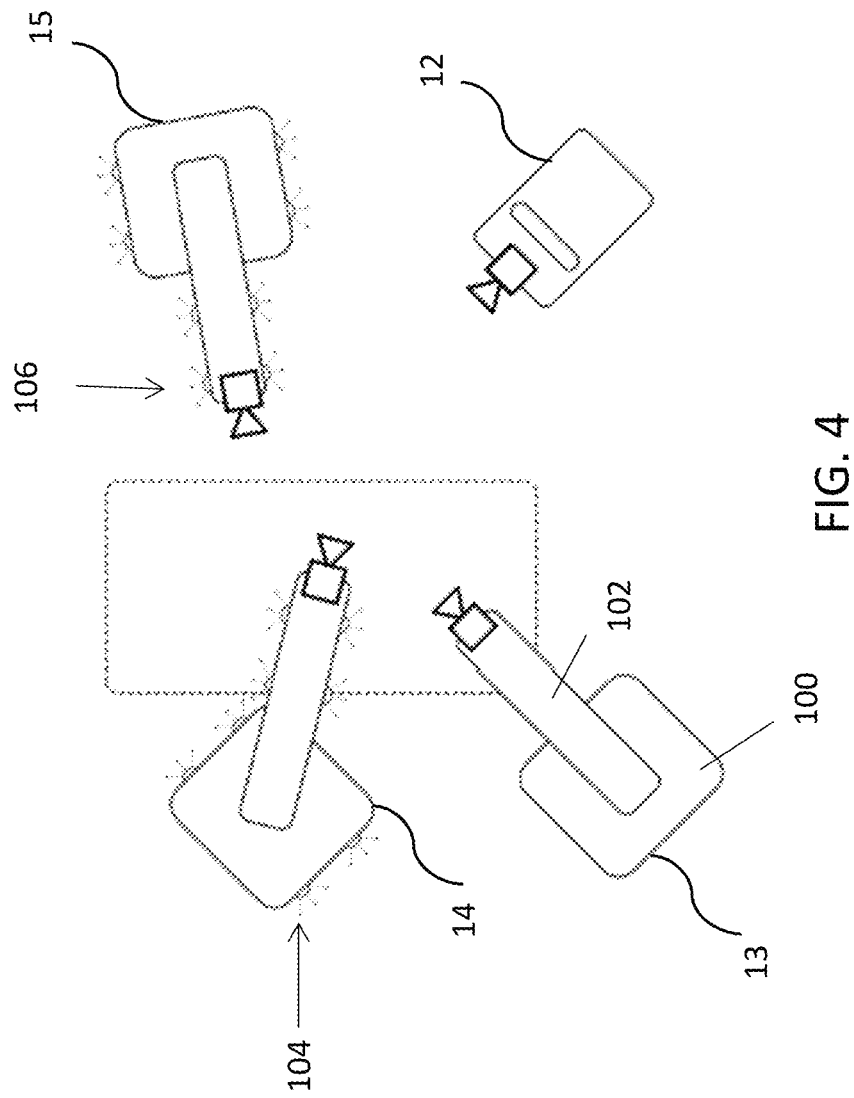
FIG. 4 shows a top plan view of an operating room using optical trackers and emitters to determine relative positions of subsystem components.

Emitters may be placed on either or both of a fixed portion of the manipulator arm, or a moveable portion of the manipulator arm. In the example shown in FIG. 4, each arm has a base 100 that remains in a fixed position while surgery is performed, and a boom 102 that may move to robotically manipulate the surgical instrument during the procedure. As shown, a first emitter or collection of emitters 104 is positioned on the (fixed) base. Emitters 104 may be spaced around the perimeter of the base 100. Where the base is multi-sided, emitters 104 may be spaced along two or more sides of the base as shown. Note that these are but examples, and that the emitters 104 may be on any part of the base 100 that remains fixed during surgery.

A second emitter or collection of emitters 106 may be positioned on a moveable part of the manipulator arm. In the drawings, the emitters 106 are shown on boom 102, but in other embodiments they might be on another moveable part of the manipulator arm. It should be understood that while FIG. 4 only shows emitters 104, 106 on two of the arms, it is contemplated that either or both emitter sets/arrays 104, 106 may be positioned on each of the arms, and emitters might also be placed on the console 12 and/or patient bed.

Where one or more emitters 104 are on a fixed portion of the manipulator, and one or more emitters 106 are on a portion of the manipulator that moves during surgery, the separation between the emitters 104 and the emitters 106 may be determined using the kinematic data from the relevant manipulator joints and the associated transformations.

To enhance visibility and to minimize line-of-sight occlusions, it may be advantageous to mount a tracker/camera to the moveable portion of the manipulator arm, such as on the boom as shown. However, where the camera is mounted to a moving portion of the manipulator, it is necessary to consider the movements on the camera (i.e., using kinematic data from the relevant manipulator joints) when performing the triangulation calculations.

The use of multiple emitters on the various subsystems lends itself well to understanding the relative positions of the subsystems even in occluding environments. If only one emitter of a subsystem (e.g., arm 14) is visible to a camera of a second subsystem (e.g., arm 15), but a second emitter of arm 14 is visible to a camera of a third subsystem (arm 13), the position or arm 14 relative to arms 15 and 13 can be determined. Since the spatial relationship between the two emitters on arm 14 is known (because they are at a fixed distance from one another, or because their spatial relationship can be determined using the known kinematics of arm 14), then the location of arm 14 can be determined using the known relative positions of arms 15 and 13.

With the disclosed system, the relative base positions of the subsystems may be determined using emitters on fixed portions of the tracked subsystems or on tracked moving portions. Kinematic data from each subsystem may be used to determine movements of that subsystem's joints and their impacts on the cameras or emitters. An internal transformation between the base and the moving camera(s)/emitter(s) on that subsystem is performed. Knowledge of the positions of the emitters/cameras for each subsystem then allows the relative positions of each subsystem base to be determined using triangulation as described above.

Figure 6C:
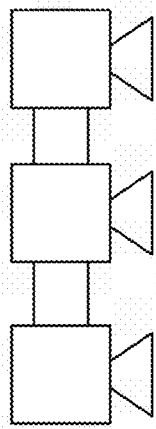
FIGS. 6A-6F illustrate exemplary tracking camera unit configurations.
Figure 6D:
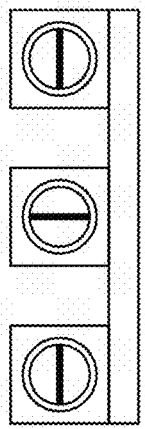
Figure 6E:
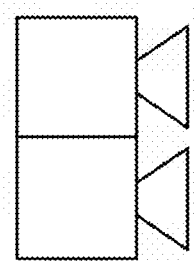
Figure 6F:
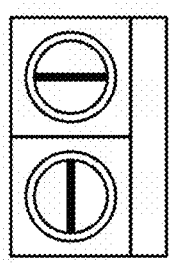
Figure 6A:
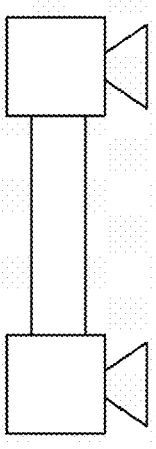
Figure 6B:
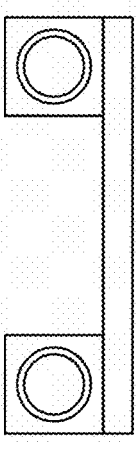

In the disclosed embodiments, the camera may comprise a tracking camera unit (TCU), which this may be a single camera/imager or a set of cameras/imagers. Referring to the top and front views of FIGS. 6A and 6B, respectively, in some cases, this may be a single stereo pair of imagers separated by a known baseline distance. In other cases, the TCU may be similar to the type manufactured by Sixdof Space, comprising a stereo pair of imagers to provide horizontal plane or depth information along with a centrally-located vertical imager to provide elevation information. See the top and front views shown in FIGS. 6C and 6D, respectively. In other configurations, the TCU may comprise a pair of imagers, one with optics to provide horizontal plane information and another to provide vertical plane information (FIGS. 6E and 6F). In some embodiments, the emitters and trackers may be combined into a single housing mounted to the relevant subsystem. In others they are separately positioned as illustrated in FIG. 5, for example.

All patents and applications referred to herein, including for purposes of priority, are incorporated herein by reference.

What is claimed is:

1. A method of determining relative positions of robotic manipulators, comprising:

positioning a first robotic manipulator in an operating room, the first robotic manipulator having at a plurality of first emitters and at least one first tracker positioned thereon positioning a second robotic manipulator in the operating room, the second robotic manipulator having a plurality of second emitters and at least one second tracker positioned thereon, positioning at least one third tracker at a fixed location in the operating room, each of the first and second robotic manipulators being independently positionable relative to the other of the first and second robotic manipulator and relative to the at least one third tracker, capturing an image of a first one of the first emitters using the at least one second tracker, capturing an image of a second one of the first emitters using the third tracker, and based on the known relative positions between the fixed location and the second robotic manipulator arm, determining a position of the first robotic manipulator.

2. The method of claim 1, wherein the fixed location is on a surgeon console.

3. The method of claim 1, wherein the fixed location is on a laparoscopic tower.

4. The method of claim 1, wherein the fixed location is on a floor mounted structure.

5. The method of claim 1, wherein the fixed location is on a ceiling.

6. The method of claim 1, wherein the fixed location is on an operating table.

7. The method of claim 1, wherein the first emitters and the second emitters are light emitters.

8. The method of claim 7, wherein the first emitters and the second emitters are infrared emitters.

9. The method of claim 8, wherein light emitted by the first emitters is differentiable from light emitted by the second emitters.

10. The method of claim 9, wherein the light emitted by the first emitters is differentiable from light emitted by the second emitters based on blink frequency.

11. The method of claim 9, wherein the light emitted by the first emitters is differentiable from light emitted by the second emitters based on blink sequence.

12. The method of claim 9, wherein the light emitted by the first emitters is differentiable from light emitted by the second emitters based on emitter light color.

13. The method of claim 9, wherein the emitters in the plurality of first emitters are spaced apart by a first distance, the emitters in the plurality of second emitters are spaced apart by a second distance different from the first distance, and wherein the light emitted by the first emitters is differentiable from light emitted by the second emitters based on the first distance and the second distance.

* * * * *